United States Patent
Clancy et al.

(10) Patent No.: US 9,332,886 B2
(45) Date of Patent: May 10, 2016

(54) FIDUCIAL PLACEMENT SYSTEM AND SPLAYED STYLET

(71) Applicant: Cook Medical Technologies LLC, Bloomington, IN (US)

(72) Inventors: Michael S. Clancy, Limerick (IE); John Neilan, Co. Galway (IE)

(73) Assignee: Cook Medical Technologies LLC, Bloomington, IN (US)

( * ) Notice: Subject to any disclaimer, the term of this patent is extended or adjusted under 35 U.S.C. 154(b) by 541 days.

(21) Appl. No.: 13/751,752

(22) Filed: Jan. 28, 2013

(65) Prior Publication Data

US 2013/0197356 A1 Aug. 1, 2013

Related U.S. Application Data

(60) Provisional application No. 61/592,188, filed on Jan. 30, 2012.

(51) Int. Cl.

| | |
|---|---|
| A61B 17/00 | (2006.01) |
| A47L 11/14 | (2006.01) |
| A61B 1/018 | (2006.01) |
| A61B 1/24 | (2006.01) |
| A61B 1/273 | (2006.01) |
| A61B 1/303 | (2006.01) |
| A61B 1/31 | (2006.01) |
| A61B 1/313 | (2006.01) |
| A61B 5/00 | (2006.01) |
| A61B 5/06 | (2006.01) |
| A61B 6/12 | (2006.01) |
| A61B 6/00 | (2006.01) |
| A61B 8/08 | (2006.01) |
| A61N 5/10 | (2006.01) |
| A47L 11/38 | (2006.01) |
| B08B 1/04 | (2006.01) |
| A46B 13/00 | (2006.01) |

(52) U.S. Cl.
CPC ............ *A47L 11/145* (2013.01); *A46B 13/008* (2013.01); *A47L 11/38* (2013.01); *A61B 1/018* (2013.01); *A61B 1/24* (2013.01); *A61B 1/2733* (2013.01); *A61B 1/303* (2013.01); *A61B 1/31* (2013.01); *A61B 1/3132* (2013.01); *A61B 5/0091* (2013.01); *A61B 5/064* (2013.01); *A61B 5/4244* (2013.01); *A61B 5/4312* (2013.01); *A61B 5/4381* (2013.01); *A61B 6/12* (2013.01); *A61B 6/502* (2013.01); *A61B 8/0841* (2013.01); *A61B 17/00234* (2013.01); *A61N 5/1039* (2013.01); *B08B 1/04* (2013.01)

(58) Field of Classification Search
CPC ......................................... A61B 1/01
See application file for complete search history.

(56) References Cited

U.S. PATENT DOCUMENTS

| | | | | |
|---|---|---|---|---|
| 2008/0306406 | A1* | 12/2008 | Thompson et al. | 600/567 |
| 2009/0209804 | A1* | 8/2009 | Seiler et al. | 600/7 |
| 2011/0152611 | A1* | 6/2011 | Ducharme et al. | 600/104 |
| 2012/0143029 | A1* | 6/2012 | Silverstein et al. | 600/374 |

* cited by examiner

*Primary Examiner* — Tse Chen
*Assistant Examiner* — Lisa Kinnard
(74) *Attorney, Agent, or Firm* — Brinks Gilson & Lione

(57) ABSTRACT

A fiducial deployment system may include one or more of a needle including a dimpled retention structure configured to releasably retain a plurality of fiducials, each of which includes a central aperture (which may be embodied as a groove or similar opening); a retention/deployment stylet that traverses through each fiducial's central aperture and releasably engages a distalmost fiducial of the plurality of fiducials with a splayed distal stylet end; a pusher cannula member; and echogenic dimpling and/or other echogenic-enhancing features on at least a distal portion of the needle.

20 Claims, 3 Drawing Sheets

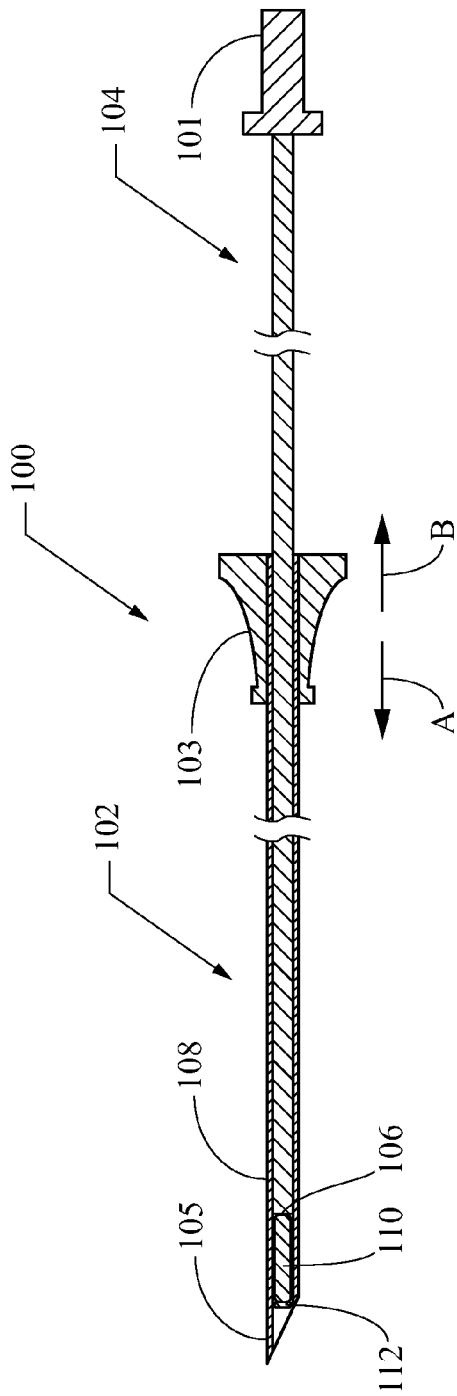
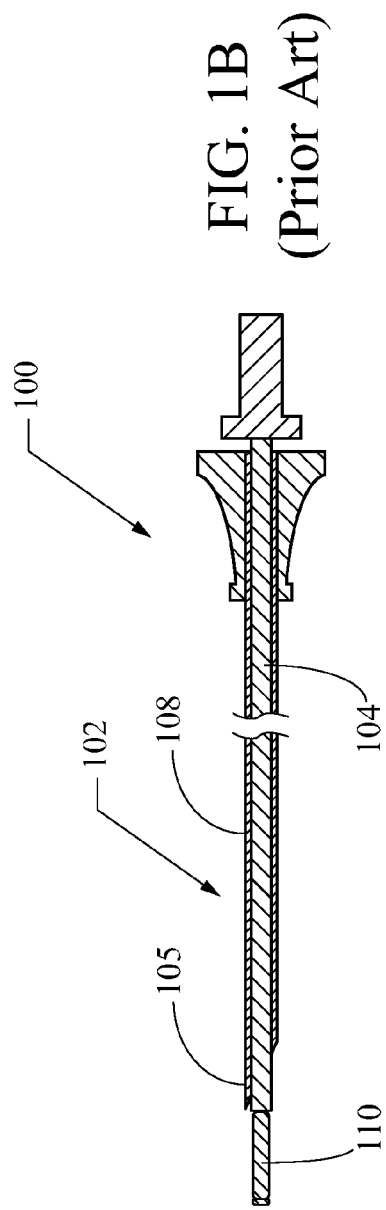
FIG. 1A
(Prior Art)
FIG. 1B
(Prior Art)

US 9,332,886 B2

FIDUCIAL PLACEMENT SYSTEM AND SPLAYED STYLET

CROSS-REFERENCE TO RELATED APPLICATIONS

This application claims priority to U.S. provisional application Ser. No. 61/592,188, filed Jan. 30, 2012, which is incorporated by reference herein in its entirety.

TECHNICAL FIELD

Embodiments disclosed herein generally relate to a medical device system including one or more fiducials and methods of use for same. More particularly, the invention pertains to specially-configured fiducials, needles configured for use with them, and methods of use for same.

BACKGROUND

Medical procedures often require locating and treating target areas within a patient. Focused, dose-delivery radiation therapy requires locating the target with a high degree of precision to limit damaging healthy tissue around the target. It is particularly important to know or be able accurately to estimate the precise location of the target in radiation oncology because it is desirable to limit the exposure of adjacent body parts to the radiation in a patient already suffering the depredations of cancer. However, in all treatment procedures, whether radiologic or otherwise, it is most desirable to be able to accurately target a region to be treated in a manner that protects the tissue and organs immediately surrounding the target location.

In many applications, it is not possible to directly view a treatment target or portion thereof (such as, for example, a cancerous tumor, cyst, pseudocyst, or other target) that needs to be acted on in some manner. As one example, when treating a lung or pancreatic tumor with radiation, it may not be possible to view the actual tumor within the patient immediately before and/or during the radiation treatment. It is therefore highly advantageous to have some mechanism for permitting the tumor to be located accurately so that the radiation treatment can be targeted at the tumor while avoiding damage to healthy tissue.

Even for target regions that may be visualized using CAT (computer-assisted tomography) scans, MRI (magnetic resonance imaging), x-rays, ultrasound, or other techniques, difficulties often arise in targeting a treatment. This is particularly true for target regions within a torso of a patient and soft tissue regions. Due to the mobility of tissues in those regions (e.g., movement of internal organs during respiration and/or digestion, the movement of breast tissue with any change of body position), a target region may not remain fixed relative to anatomical landmarks and/or to marks that can be placed onto an external surface of a patient's body during one of those visualization procedures.

Several techniques have been developed to address this problem. One such technique is to place markers into the patient along the margins of the target region. The markers may be active (e.g., emitting some kind of signal useful in targeting a therapy) or passive (e.g., non-ferromagnetic gold markers—called fiducials—that can be used for targeting under ultrasound, MRI, x-ray, or other targeting techniques, which may be included in a treatment device such as a targeted-beam radiation device).

A fiducial typically is formed of a radio-opaque material so that the target can be effectively located and treated with a device that targets a site using the fiducials as positional markers under radiographic detection. Typically, a plurality of fiducials providing for three-dimensional orientation of targeted visualization and/or therapy may be inserted into the patient during a simple operation. Percutaneous placement is most commonly used. For example, percutaneous placement of fiducials along the margins of a pancreatic tumor is a common technique for facilitating radiation treatment of the tumor. However, the procedure can be complex and painful (particularly for obese patients, where the needle size is necessarily larger). Another process using percutaneously implanted objects in a patient is brachytherapy. In brachytherapy, radioactive sources or "seeds" are implanted into and/or adjacent a tumor to provide a high dose of radiation to the tumor, but not the healthy tissue surrounding the tumor. Techniques for minimally-invasive placement via an endoscope have recently been developed for fiducial placement into a patient's internal organs.

FIGS. 1A and 1B show longitudinal sectional views of a two-piece introducer 100 of the prior art useful for placement of brachytherapy seeds or fiducials. Referring first to FIG. 1A, the introducer 100 includes a needle 102 and a stylet 104 slidably disposed within the needle 102. The stylet 104 includes a first handle 101 and a blunt distal end 106. The needle 102 includes a second handle 103 and a bevel-tipped cannula 108 extending through the second handle 103. The cannula 108 is configured to hold a seed/fiducial 110. The cannula 108 has a distal tip 105 configured for percutaneous implantation of the seed/fiducial 110 into the patient.

In a "pre-loaded configuration," the seed/fiducial 110 is retained in the cannula 108 by a plug 112 made from bone wax or other suitable bio-compatible material(s). This is typically accomplished by a "muzzle-loading" technique where the fiducial is placed into the distal end of the needle and then held in place by the bone wax plug. This can present some challenges, as the bone wax plug 112 can be visible as an artifact in the patient, potentially interfering with clear visualization of body structures or treatment devices. With this configuration, the cannula 108 must be withdrawn and reloaded after delivery of each seed/fiducial 110. If the target locations for the fiducials are very far apart, use of a single percutaneous introducer cannula/trocar for multiple introductions of the cannula 108 may not be possible. In such a circumstance, the patient must endure several percutaneous punctures (and the increased attendant risk of infection for each).

To implant the desired arrangement of seeds/fiducials 110 at a target location in a patient, an operator pushes the cannula 108 in a first direction (arrow A) to insert the tip 105 into the patient (typically under fluoroscopic visualization). The operator then pushes the second handle 103 further in the first direction to position the tip 105 at the desired depth within the patient where a seed/fiducial 110 is to be implanted. Throughout this motion, the operator moves the needle 102 and the stylet 104 together as a unit. At the desired depth/location, the operator grasps the first handle 101 with one hand and the second handle 103 with the other hand. Then, the operator holds the first handle 101 stationary while simultaneously sliding the second handle 103 back in a second direction (arrow B) toward the first handle 101. As shown in FIG. 1B, this movement causes the cannula 108 to retract over the seed/fiducial 110 to implant it in the patient. Alternatively, the operator may move the first handle 101 in the first direction (arrow A) while sliding the second handle 103 back in the second direction (arrow B) or holding it stationary. This causes the stylet 104 to push the seeds 110 out of the cannula 108. The procedure is then repeated to place other seeds/ fiducials 110. When being used for targeting of radiation therapy, a minimum of three fiducials is typically required.

As will be appreciated from the disclosed structure, after deploying one fiducial, one may alternatively reload the introducer 100 from the proximal end by completely withdrawing the stylet 104, then placing another fiducial into the needle lumen and advancing it therethrough to a second location to which the distal needle tip 105 has been directed (a "breech-loading" technique). Provided that the fiducial target sites are sufficiently close together to allow this technique, it can reduce the number of percutaneous punctures or other access procedures needed to place more than one fiducial. However, it creates a problem for procedures where ultrasound is being used or is to be used in the near-future because it introduces air pockets into the tissue and related fluids. Those air pockets with tissue and/or fluid are echogenic in a manner that can interfere with ultrasound visualization of a target area and/or tools being used to diagnose or treat in/around the area. In some brachytherapy techniques, a series of fiducials may be preloaded into the needle—either separately or connected by a suture or similar device—then placed together in fairly close proximity; however, such a technique typically is not effective for placing three or more fiducials in sufficiently disparate locations to use for targeting a treatment relative to, for example, margins of a tumor.

The process is similar when implemented endoscopically in the manner developed rather recently, except that the needle and stylet are of the type known in the art for use through the working channel of an endoscope. One limitation of current endoscopic techniques is the size of fiducial that can be introduced. With the size limitation of endoscope working channels, the largest needle that can typically be used without risking bending, crimping, curving or otherwise damaging a needle (that does not have an internal stylet or other support) during advancement out of the endoscope to an anatomical target is a 19-gauge needle. This limits the size of the fiducial that can be introduced through the needle lumen using current, cylindrical fiducials. The endoscopic technique generally suffers from the same reloading problems as described above. Even though the external percutaneous punctures are not an issue, having to withdraw and reload takes up valuable time and complicates the procedure, potentially requiring additional personnel, whether only the stylet is withdrawn for "breech-loading" or the entire device is withdrawn for "muzzle-loading."

It would be desirable to use ultrasound, and particularly endoscopic ultrasound (EUS) for navigation and placement of fiducials. As such it would be desirable to provide and use the largest possible fiducial that will provide improved echogenicity based on its size and echogenic profile. It would be desirable to provide multiple fiducials in a needle that can be introduced in a controlled serial manner (one at a time) rather than requiring manual reloading after placement of each fiducial.

BRIEF SUMMARY

Embodiments of a fiducial deployment system described herein may include one or more of a needle including a dimpled retention means configured to releasably retain a plurality of fiducials, each of which includes a central aperture (which may be embodied as a groove or similar opening); a retention/deployment stylet that traverses through each fiducial's central aperture and releasably engages a distal-most fiducial of the plurality of fiducials; a pusher cannula member; and echogenic dimpling and/or other echogenic-enhancing features on at least a distal portion of the needle.

BRIEF DESCRIPTION OF THE DRAWINGS

FIGS. 1A-1B show a prior art fiducial introducer and method of use.

DETAILED DESCRIPTION

Figure 2:
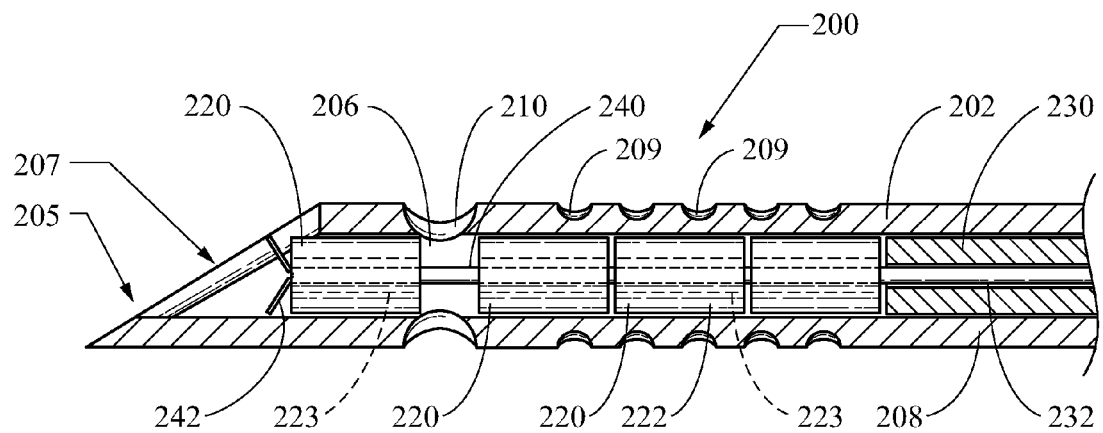
FIGS. 2-2D shows one embodiment of a fiducial deployment system with a method of use.

The terms "proximal" and "distal" are used herein in the common usage sense where they refer respectively to a handle/doctor-end of a device or related object and a tool/patient-end of a device or related object. Certain embodiments may be configured for placement of fiducials through an endoscope. More particularly, in certain embodiments, a fiducial placement system may be configured of sufficient length and flexibility for use and actuation through a working channel of a gastrointestinal endoscope providing access to the gastrointestinal tract and/or adjacent structures in a patient body, and/or a fiducial placement system may be configured for percutaneous fiducial deployment.

Embodiments are described with reference to the drawings in which like elements are generally referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly. The present embodiments provide multiple fiducials in a needle that can be introduced in a controlled serial manner (one at a time) rather than requiring manual reloading after placement of each fiducial, and that also prevent the jackknifing/train-wreck effect of multiple fiducials being deployed at the same time in the manner used by prior art devices.

A fiducial deployment system 200 is described with reference to FIG. 2. The system 200 includes a needle 202 that includes a generally tubular cannula body 208. The cannula 208 in this embodiment includes a beveled distal tip 205 configured for penetrating tissue and directing the cannula's contents to a target location, but other embodiments may include non-beveled tips or other designs. The body 208 defines a needle lumen 206 that extends longitudinally through at least a lengthwise portion of the cannula body to a distal needle end opening 207.

An outer surface of the cannula body 208 is dimpled (see sample dimples 209) to enhance its ability to reflect ultrasound waves and thereby provide a desirable echogenic profile. This dimpled characteristic may be embodied as a different irregular, patterned, or textured surface feature (e.g., knurled, ribbed) that may enhance the echogenicity of the cannula 208, which will aid in visualizing it during EUS-guided placement, and allow it to be used in ultrasound visualization of a target site (e.g., a tumor) being marked by one or more fiducials. Other echogenic enhancements may be provided in addition to, or instead of, the dimpling. For example, certain echogenic polymers may be used in the cannula construction, or as a coating of a metal cannula. Other echogenic enhancements known in the art may be implemented within the scope of the claims. The dimpled or otherwise echogenically-enhanced region preferably will include a distal needle end region, while a more proximal length of the needle may be free of dimples and/or other echogenicity-enhancing features.

At least one substantially inflexible detent 210 may be provided as a protrusion extending radially into the needle lumen 206. The detent here is embodied as a pair of deeper dimples 210 that provide a restricted region of smaller internal diameter for the needle lumen 206 than is provided for the inner diameter of the lumen's major length proximal of the detent 210. In other embodiments, the detent 210 may not include an externally visible dimple, and/or it may include one, two, three, or more protrusions into the needle lumen 206. In still other embodiments, a needle embodiment may not include any protrusion, such that the needle lumen is of a substantially consistent inner diameter, at least along its distal length (although, a proximal length that will not hold fiducials may have a smaller inner and/or outer diameter.

Figure 3A:
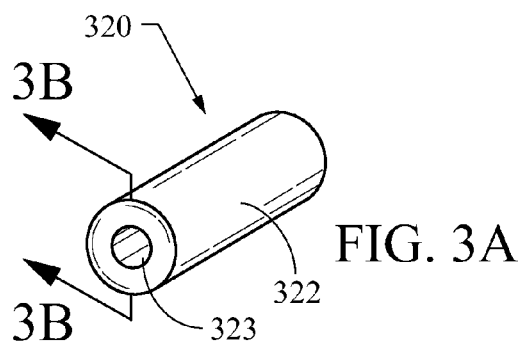
FIGS. 3A-3B show a tubular embodiment of a fiducial useful with the system of FIG. 2.
Figure 3B:
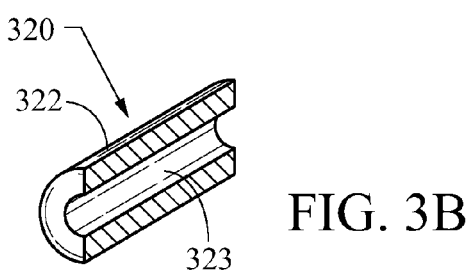
Figure 4:
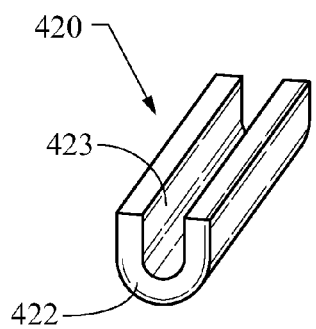
FIG. 4 shows another embodiment of a fiducial useful with the system of FIG. 2.

At least one fiducial, embodied here as a plurality of fiducials 220 may be included in the needle lumen 206. Each of the fiducials 220 may include a generally columnar body 222 slidably disposed in the needle lumen 206. The body 222 may be substantially solid, substantially hollow, or otherwise configured in any manner appropriate for providing a desirable fluoroscopic identifiability of the fiducial 220. FIGS. 3A-3B and 4, discussed below, show two embodiments preferred for use with the presently disclosed system. The fiducial body 222 includes a fiducial aperture 223 extending longitudinally therethrough.

Fiducials 220 (and other fiducial embodiments described herein) preferably will be formed of a radio-opaque, non-ferromagnetic material such as, for example, gold, platinum, palladium, iridium, tantalum, or alloys thereof, with one preferred embodiment including an alloy of palladium with rhenium (advantages of which may include desirable radio-opacity, market-price stability superior to gold, and ultrasound-reflectivity/echogenicity due to density). Being radio-opaque will allow the fiducial to be used in deployment techniques using fluoroscopy, as well as making it detectible/visualizable by radiographic means during a treatment or other procedure where it may be desirable to know the location(s) of one or more fiducials. Being non-ferromagnetic will lessen the likelihood that visualization techniques or other procedures employing magnetic fields such as, for example, MRI, will re-orient or otherwise dislodge a fiducial. Echogenic construction of a fiducial or needle may be enhanced by surface texture, but can also be provided by structural inclusions such as embedded bubbles or beads that provide for a different ultrasound reflectivity than material surrounding them. Fiducials may also be coated with a material (e.g., parylene) configured to reduce backscatter during radiography. In one embodiment, certain fiducials may generally be hollow (e.g., having an aperture or lumen occupying a major internal volume).

An elongate pusher member 230 extends longitudinally through the needle lumen 206 and contacts a proximal-most of the fiducials 220. The pusher 230 is configured to push the fiducials distally and/or to prevent them from migrating proximally within the needle lumen 206. The pusher 230 includes a pusher lumen 232, which may be enclosed (e.g., in an embodiment where the pusher is formed as a tubular pusher cannula) or open along some portion (e.g., in an embodiment where the pusher is formed with a c-shaped or u-shaped cross-section).

An elongate stylet 240 extends through the pusher lumen 232 and through the fiducial aperture 223 of the fiducial(s) 220. The distal end of the stylet 240 is collapsibly splayed. That is, the stylet 240 includes at least one splayed distal end portion 242 that is reversibly bent or hinged out of the longitudinal axis of the stylet 240. This splayed portion may include one, two, three, or more splayed-out portions of the stylet, which may all be at the distal end, and/or which may be longitudinally spaced along the stylet length near the distal end. The splayed portion 242 may be configured as biased-apart jaws, biased-apart prongs, or other structures within the skill in the art that will be collapsible and capable of efficiently performing the method described herein.

In one preferred embodiment, the splayed portion 242 includes a transverse split at the distal end of the stylet 240 forming two distally-splayed members (biased apart) that provide an outer diameter larger than both the outer stylet diameter and the inner fiducial aperture diameter. In this manner, as shown in FIG. 2, the splayed portion 242 can help distally retain a distalmost fiducial 220. And, as shown with reference to the method illustrated in FIGS. 2-2D, the splayed portion 242 can be collapsed and drawn through the aperture 223 of a fiducial, then—as the biased-apart splayed members are freed from constriction of the aperture 223—re-opened and used to push the distalmost fiducial past the protrusions 210 to deploy that fiducial 220. As such, the stylet 240 is configured to releasably retain and to assist in deploying the fiducials 220.

Figure 2A:
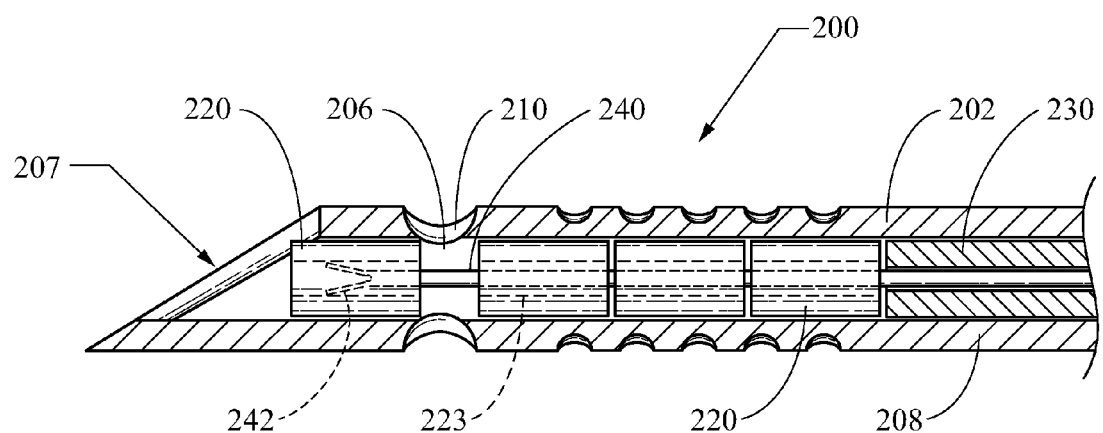
Figure 2B:
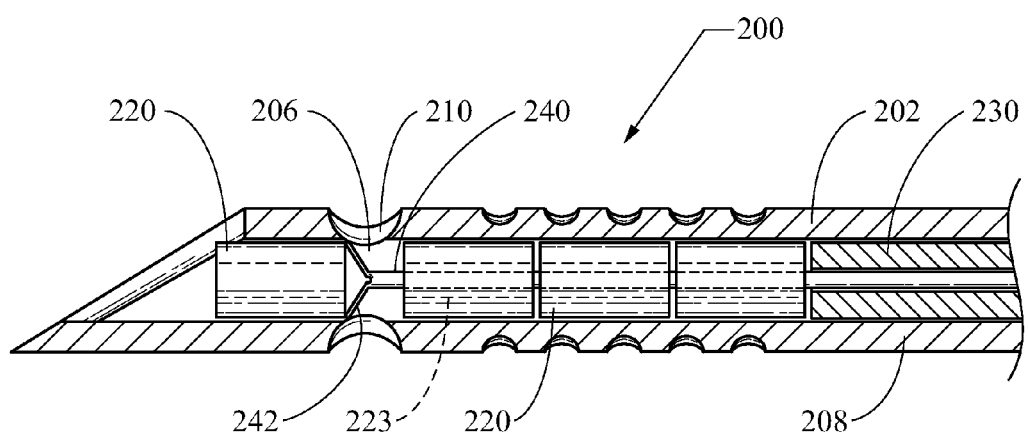
Figure 2C:
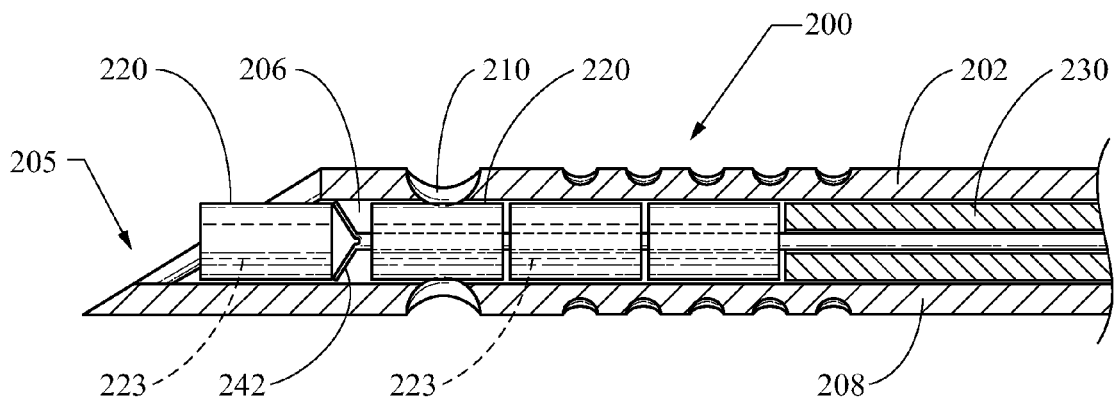
Figure 2D:
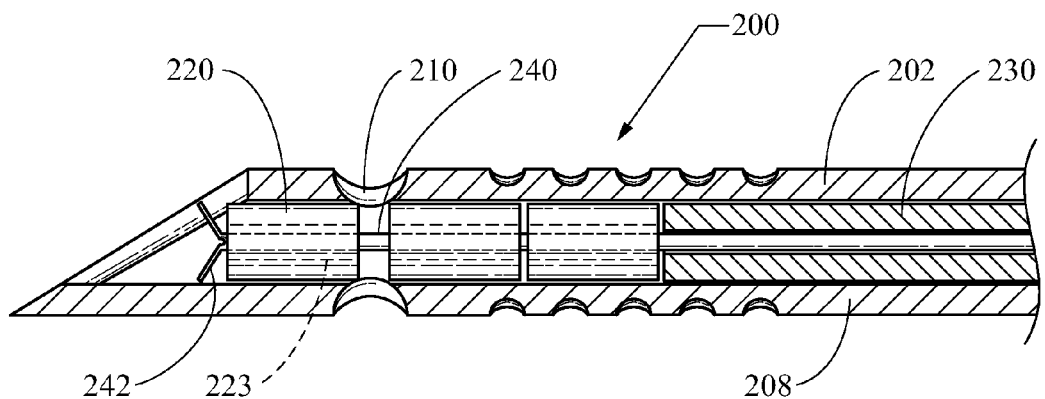

A method of fiducial deployment is also described with reference to FIGS. 2-2D. As described above, FIG. 2 shows a fiducial deployment system. A distalmost fiducial 220 is positioned within the beveled needle portion distal of the retention protrusions 210. That distalmost fiducial 220 is retained by the splayed end 242 of the stylet 240. Then, as shown in FIG. 2A, the stylet 240 is drawn proximally so that the splayed distal end portion 242 is collapsed in the fiducial aperture 223. FIG. 2B shows that when the stylet splayed distal end portion 242 is drawn completely through the fiducial aperture 223, it re-expands (due to its open bias) to contact the proximal end of the distalmost fiducial 220. The stylet 240 may then be advanced distally to deploy the distalmost fiducial 220 out of the distal end of the needle 202.

The deployment may also (or instead) include holding the stylet 240 relatively stationary and retracting the needle 202 from the fiducial 220 to leave it in a particular location. That is, in one aspect, a fiducial deployment may be accomplished by positioning the distal needle end 205 and a distalmost fiducial 220 therein at a first target location, then retracting the needle 202 while retaining the position of the stylet 240 such that the distalmost fiducial 220 exits the needle 202, and remains in a desired first target position. In another aspect, a fiducial deployment may be accomplished by positioning the distal needle end 205 and the distalmost fiducial 220 therein adjacent a first target, then holding the needle 202 in position while advancing the stylet 240 such that the fiducial 220 is advanced out of the needle end 205, and into a desired first target position.

A handle (not shown) may be provided that will provide tactile, auditory, and/or visual indicia regarding deployment of a fiducial. When the needle end 205 is in a desired position, the user can advance the stylet 240, and thereby the distalmost fiducial, into the target site. The next fiducial in line will be stopped as it engages the detent 210. In embodiments lacking the detent(s) 210, the user may rely upon the splayed stylet end 242 to retain successive fiducials until such time as is desired to deploy that next fiducial in line. Such embodiments will readily be envisioned by one of skill in the art with reference to FIG. 2, excepting that—in such embodiments—the protrusions 210 will be absent. The needle may then be repositioned without having to be fully withdrawn from the patient. Next, as shown in FIG. 2D, the pusher 230 may be used to distally advance the fiducial(s) so that the now distal-most fiducial is pushed past the protrusions 210 and is ready for deployment in the manner described above (before, during, or after any needle repositioning). Although four fiducials are shown in FIGS. 2-2C, it should be appreciated that more or fewer fiducials may be provided in a pre-loaded needle. It will often be preferred that the fiducials be proportioned such that complete deployment of a distalmost fiducial will include it substantially clearing the distal needle tip 205.

As noted above, after deploying a distalmost fiducial, the user may retract the needle 202 from the first target site, and then direct it to a second target site, where the procedure described above may be repeated. These steps may be repeated for placement of third, fourth, and further fiducials. As is known in the art, these fiducials may be used for "positive targeting" and/or "negative targeting" of a therapy such as radiation therapy ("positive targeting" indicating "treat here", and "negative targeting" indicating "do not treat here"). The present system presents numerous advantages. For example, consider a patient already undergoing an endoscopy procedure to biopsy a located but undiagnosed tissue mass. The endoscopic biopsy can be taken and a tissue slide prepared immediately. If a diagnosis is made (in conjunction with whatever other data are available and pertinent) that the tissue mass will benefit from a treatment where placement of fiducials is indicated, the physician can immediately deploy fiducials in the manner described above, potentially using the same endoscope already positioned for the biopsy.

FIGS. 3A-3B show an embodiment of a fiducial 320 useful with the system described above. The fiducial 320 includes a generally tubular body 322 fully encompassing a longitudinal fiducial aperture 323 configured to allow passage therethrough of the stylet 230. FIG. 3B shows a longitudinal section view of the fiducial 320 depicted in FIG. 3A.

FIG. 4 shows an embodiment of a fiducial 420 useful with the system described above. The fiducial 420 includes a body 422 with a generally U-shaped cross section that less-than-fully encompasses a longitudinal fiducial aperture 423 configured to allow passage therethrough of the stylet 230. It should be appreciated that other embodiments may be practiced consistent with the scope of the present disclosure (e.g., including a C-shaped cross-section, with rectilinear geometry, or other configurations of fiducials with an aperture configured to allow the stylet-based deployment described above).

Drawings and particular features in the figures illustrating various embodiments are not necessarily to scale. For example, it will generally be desirable that the tolerances (e.g., relative internal and external diameters of the needle lumen, pusher body and lumen, fiducial body and aperture, and stylet) be very close so that the components use space and materials as efficiently as possible. Some drawings may have certain details magnified for emphasis, and any different numbers or proportions of parts should not be read as limiting, unless so-designated by one or more claims. Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. For example, a needle and fiducials of the present system may be used percutaneously, including in another mini-mally invasive surgical procedure, such as a laparoscopic-type procedure, within the scope of the claimed invention. For example, a target site may be a location in or near the gastrointestinal tract (e.g., liver, pancreas) such as those locations that may be accessible by endoscopy (using a minimally invasive endoscope introduced through a natural patient orifice, e.g., mouth, anus, vagina). This includes—more broadly—sites reachable through NOTES (natural orifice translumenal endoscopic surgery) procedures, but also includes other body regions (e.g., liver, prostate, breast, tonsil) not necessarily associated with the gastrointestinal tract. The present method and device may also be used with other minimally-invasive surgical techniques such as percutaneous endoscopic procedures (e.g., laparoscopic procedures) or percutaneous non-endoscopic procedures, but most preferably is used with less invasive endoscopy procedures. It is therefore intended that the foregoing detailed description be regarded as illustrative rather than limiting. And, it should be understood that the following claims, including all equivalents, are intended to define the spirit and scope of this invention.

We claim:

1. A fiducial deployment system comprising:
a needle including
a generally tubular cannula body defining a needle lumen disposed through at least a lengthwise portion of the cannula body and
a distal needle end region, the distal end region comprising
a distal needle end opening at a distal end of the needle lumen;
at least one fiducial comprising a fiducial body slidably disposed in the needle lumen, which fiducial body includes a fiducial aperture extending longitudinally therethrough;
a pusher slidably disposed longitudinally through the needle lumen proximal of and contacting the at least one fiducial, where the pusher is configured to advance the at least one fiducial out of the distal needle end opening; and
a stylet including at least one splayed distal end portion, the stylet extending longitudinally through a portion of the needle lumen and through the aperture of the at least one fiducial,
wherein the at least one splayed distal end portion is biased apart and engaging a distal end surface of the at least one fiducial to releasably retain the at least one fiducial, and the at least one splayed distal end portion is sufficiently collapsible to pass proximally through a cross-sectional area of the fiducial aperture to release the at least one retained fiducial.

2. The fiducial deployment system of claim 1, where the pusher is embodied as a pusher cannula including a pusher lumen longitudinally disposed therethrough, through which a portion of the stylet slidably extends.

3. The fiducial deployment system of claim 2, where the pusher cannula includes a tubular length encompassing the pusher lumen.

4. The fiducial deployment system of claim 1, where the at least one fiducial comprises a generally cylindrical portion.

5. The fiducial deployment system of claim 1, where the needle comprises at least one echogenically-enhanced region.

6. The fiducial deployment system of claim 1, further comprising at least one protrusion configured as a retaining detent extending radially into the needle lumen to form a restricted inner diameter that is less than an inner diameter of a major length of the needle lumen, where the at least one needle protrusion is provided by a dimple in the tubular cannula body.

7. The fiducial deployment system of claim 6, where the stylet at least one splayed distal end portion is configured to engage a proximal surface of the at least one fiducial and pushingly advance the at least one fiducial distally through the needle lumen past the at least one protrusion.

8. The fiducial deployment system of claim 1, where the at least one fiducial comprises a plurality of fiducials, each including a proximal fiducial end and a distal fiducial end, where the proximal end of at least one of the fiducials is immediately adjacent the distal end of another of the fiducials.

9. The fiducial deployment system of claim 1, where the at least one splayed portion comprises a generally transverse split in a distal end of the stylet.

10. The fiducial deployment system of claim 1, where the needle is configured as an endoscopic needle having sufficient length and flexibility for effective deployment through a trans-esophageal gastrointestinal endoscope.

11. The fiducial deployment system of claim 1, where the needle is configured as a percutaneous needle.

12. The fiducial deployment system of claim 1, where the fiducial body includes a tubular length encompassing the fiducial aperture.

13. The fiducial deployment system of claim 1, where the fiducial body includes a length having a U-shaped cross-section partially encompassing the fiducial aperture.

14. The fiducial deployment system of claim 1, where the at least one splayed portion is configured as biased-apart jaws.

15. The fiducial deployment system of claim 1, where the at least one fiducial body is substantially hollow.

16. A method of deploying a fiducial with the fiducial deployment system of claim 1, said method comprising steps of:
  providing the fiducial deployment system of claim 1;
  directing the distal needle end region to a target location; and
  retracting proximally the stylet's at least one splayed distal end portion through the aperture of the at least one fiducial to release the at least one fiducial from the stylet.

17. The method of claim 16, further comprising a step of advancing the stylet distally relative to the needle to direct the at least one fiducial out of the distal needle end region.

18. The method of claim 16, further comprising a step of retracting the needle proximally relative to the stylet to release the at least one fiducial out of the distal needle end region.

19. The method of claim 16, where the system according to claim 1 further comprises at least one protrusion configured as a retaining detent extending radially into the needle lumen to form a restricted inner diameter that is less than an inner diameter of a major length of the needle lumen, and; where the at least one fiducial further comprises a first distalmost fiducial and a proximally adjacent second fiducial, where the retracting step comprises retracting the at least one splayed distal end only through the fiducial aperture of the distalmost fiducial, and where the method further comprises a step of advancing the second fiducial past the at least one protrusion while retaining it with the at least one splayed distal end of the stylet.

20. A fiducial deployment system comprising:
  a needle including a generally tubular body defining a longitudinal needle lumen through the entire needle length;
  where a distal needle end region of the needle includes a retaining detent extending radially into the needle lumen to form a restricted inner diameter that is less than an inner diameter of a major length of the needle lumen;
  a plurality of tubular fiducials each comprising a fiducial body slidably disposed longitudinally aligned distally to proximally in the needle lumen, each fiducial body including a fiducial aperture extending longitudinally therethrough;
  a pusher cannula slidably disposed longitudinally through the needle lumen proximal of and contacting a proximal-most one of the fiducials, the pusher cannula including a pusher lumen longitudinally disposed therethrough, where the pusher is configured to advance the fiducials past the at least one protrusion and out of the distal needle end opening; and
  a stylet including at least one splayed distal end portion, the stylet extending longitudinally through a portion of the needle lumen, a portion of the pusher lumen, and the aperture of at least one of the fiducials,
  wherein the at least one splayed distal end portion is biased apart and engaging a distal end surface of the at least one of the fiducials to releasably retain the at least one of the fiducials, and the at least one splayed distal end portion is sufficiently collapsible to pass proximally through a cross-sectional area of the fiducial aperture to release the at least one of the fiducials that is retained.

* * * * *